US010189801B1

United States Patent
Yang et al.

(10) Patent No.: US 10,189,801 B1
(45) Date of Patent: Jan. 29, 2019

(54) METHOD FOR SYNTHESIZING TETRAHYDROISOQUINOLINE THIAZOLIDINE

(71) Applicant: National Chi Nan University, Nantou County (TW)

(72) Inventors: Te-Fang Yang, Taichung (TW); Sheng-Han Huang, Taichung (TW); Yan-Liang Lin, Taichung (TW); Yu-Wei Shih, Taichung (TW); Yi-Pang Chiu, New Taipei (TW)

(73) Assignee: NATIONAL CHI NAN UNIVERSITY, Nantou County (TW)

( * ) Notice: Subject to any disclaimer, the term of this patent is extended or adjusted under 35 U.S.C. 154(b) by 0 days.

(21) Appl. No.: 15/900,117

(22) Filed: Feb. 20, 2018

(30) Foreign Application Priority Data

Nov. 14, 2017 (TW) .............................. 106139231 A

(51) Int. Cl.
*C07D 277/60* (2006.01)
(52) U.S. Cl.
CPC ................................. *C07D 277/60* (2013.01)
(58) Field of Classification Search
CPC .................................................... C07D 277/60
See application file for complete search history.

(56) References Cited

FOREIGN PATENT DOCUMENTS

TW    I323659 B    4/2010

OTHER PUBLICATIONS

Inaki Osante, M. Isabel Collado, Ester Lete, and Nuria Sotmayor Stereodivergent Synthesis of Hetero-Fused Isoquinolines by Acyliminium and Metallation Methods, European Journal of Organic Chemistry, Mar. 1, 2001, pp. 1267-1277, Jul. 2001, Weinheim, Germany.
Xuyuan Gu, Scott Cowell, Jinfa Ying, et al., Synthesis of beta-phenyl-delta, epsilon-unsaturated amino acids and stereoselective introduction of side chain groups into [4,3,0]-bicyclic Beta-turn dipeptides, Tetrahedron Letters, Science Direct, 44 (2003) 5863-5866.
Maria D. Rozwadowska and Agnieszka Sulima, Synthesis and spectroscopic studies of some hydrogenated thiazolo [2,3-a]isoquinolines, Tetrahedron 57, (2001) 3499-3506.

*Primary Examiner* — Valerie Rodriguez-Garcia
(74) *Attorney, Agent, or Firm* — Muncy, Geissler, Olds & Lowe, P.C.

(57) ABSTRACT

The present invention relates to a method for synthesizing tetrahydroisoquinoline thiazolidine, which can be conducted under a relatively mild reaction condition and can rapidly synthesize tetrahydroisoquinoline thiazolidine.

7 Claims, No Drawings

METHOD FOR SYNTHESIZING TETRAHYDROISOQUINOLINE THIAZOLIDINE

FIELD OF THE INVENTION

The present invention relates to a method for synthesizing a thiazolidine compound, and more particularly relates to a method capable of synthesizing tetrahydroisoquinoline thiazolidine under a relatively mild reaction condition.

BACKGROUND OF THE INVENTION

Many thiazolidine compounds are used as important architectures of drugs due to biological activities thereof. For example, Taiwan patent No. 1323659 provides a novel thiazolidin-4-one derivative, which can be used as an immunosuppressive agent that achieves the aim of an immunosuppressive effect effectively and durably by reducing the number of T lymphocytes and B lymphocytes cycles and infiltration.

With respect to synthesizing method of thiazolidine compounds, Rozwadowska et al. published a method in 2001, reacting an isoquinoline (formula 1) with thioglycolic acid through cycloaddition reaction to synthesize a thiazolidinedione (formula 2), and meanwhile they tried to obtain a thiazolidine derivative (formula 3) by reacting the isoquinoline (formula 1) with thiirane. However, the time of synthesis reaction was as long as 30 hours, and the productivity is also not very ideal (32%). (Rozwadowska, M. D.; Sulima, A. Tetrahedron 2001, 57, 3499-3506)

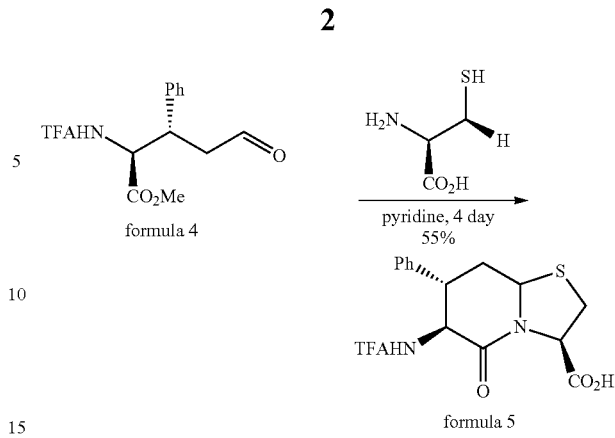

Additionally, as published in 2001, Osante et al. studied a cyclization method of a heterocyclic molecule, in which the author obtained a compound (formula 7) through a cycloaddition reaction after using the compound thiazolidinedione (formula 6) as the starting material and deprotonating the benzene ring under a strong alkaline condition. Although the synthesis conditions disclosed in this literature improved the reaction time greatly, but the reaction had to be conducted under the strong alkaline condition and the preparation steps of the starting material were also very complicated, and in addition the productivity was also not very high as only 49%. (Osante, I.; Collado, M. I.; Lete, E.; Sotomayor, N. Eu. J. Org. Chem. 2001, 1267-1277)

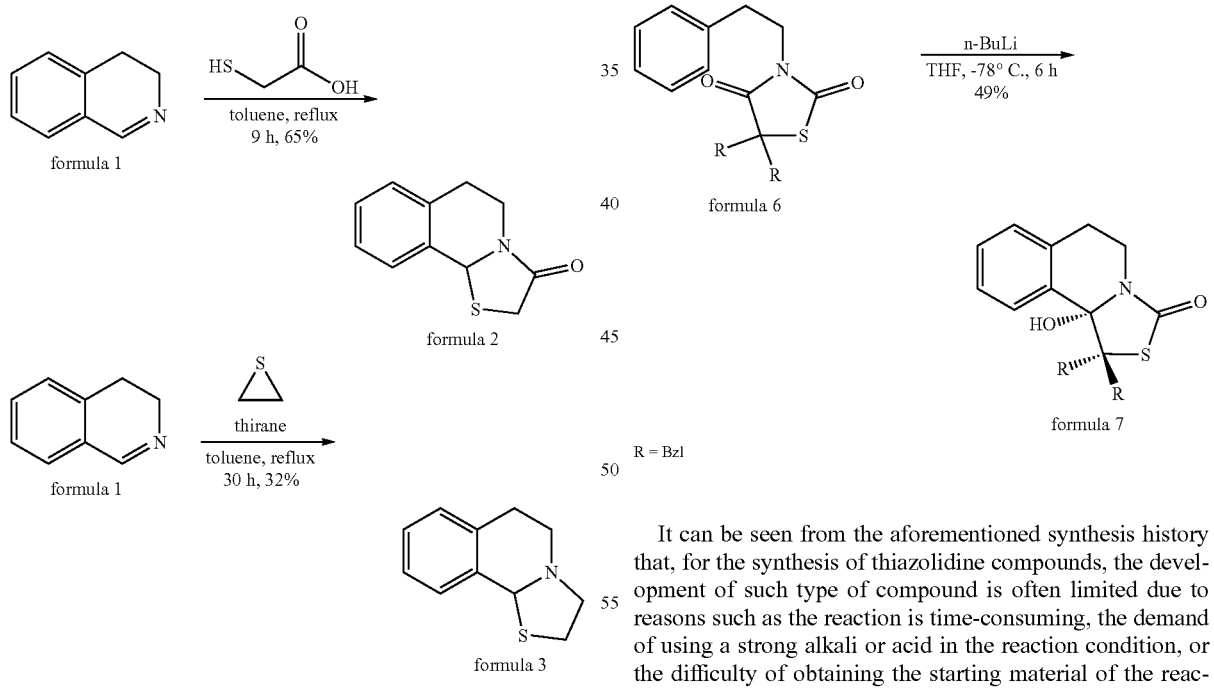

In 2003, Gu, X. et al. published a method that reacts an amino acid with an aldehyde compound (formula 4) through cycloaddition reaction to synthesize a thiazolidine derivative (formula 5), but the required reaction time is 4 days while the productivity is only 55%. Thus there can still improve the way of synthesizing route. (Gu, X.; Cowell, S.; Ying, J.; Tang, X.; Hruby, V. J. Tetrahedron Lett. 2003, 44, 5863-5866)

It can be seen from the aforementioned synthesis history that, for the synthesis of thiazolidine compounds, the development of such type of compound is often limited due to reasons such as the reaction is time-consuming, the demand of using a strong alkali or acid in the reaction condition, or the difficulty of obtaining the starting material of the reaction. In view of this, it is an urgent need to develop a synthesis method which can meet the industry demands, so as to solve the choke points encountered during current development of thiazolidine compounds.

SUMMARY OF THE INVENTION

The main objective of the present invention is to solve defects of conventional thiazolidine compounds that during synthesis the reaction is time-consuming, the reaction conditions are strict, and the preparation of the reaction starting material is difficult.

In order to achieve the aforementioned objective, the present invention provides a method for synthesizing tetrahydroisoquinoline thiazolidine under a relatively mild reaction condition, which not only provides milder synthesis conditions, simple and fast synthesis steps, but also provides great stereoselectivity and productivity, thereby being capable of lowering the threshold of synthesis technology and cost of synthesis, and meeting the green chemical concept advocated currently.

An embodiment of the present invention provides a method for synthesizing tetrahydroisoquinoline thiazolidine, in which a compound 1a and a compound 1b are reacted at a temperature between 20° C. and 100° C. in a solvent, wherein the compound 1a comprises a structure of Formula (I), and the compound 1b comprises a structure of Formula (II):

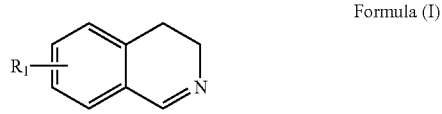

Formula (I)

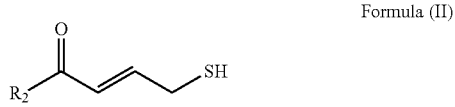

Formula (II)

In this embodiment, $R_1$ is selected from the group consisting of hydrogen, halogen, an alkyl group, and an alkoxy group; and $R_2$ is selected from the group consisting of an alkoxy group, an aryloxy group, and N(OMe)Me, wherein Me is a methyl group.

In an embodiment of the present invention, the solvent is selected from the group consisting of tetrahydrofuran (THF), ethyl acetate (EtOAc), acetone, ethanol, dichloromethane (DCM), acetone, and acetonitrile.

In an embodiment of the present invention, the reaction formula is as follows:

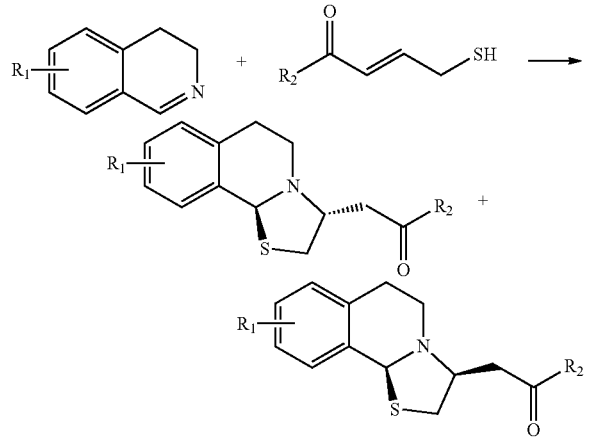

Therefore, as compared with the prior art which obtained thiazolidine compounds with a satisfactory yield only in a strict environment or after a long reaction time, the method provided by the present invention not only provides milder synthesis conditions, simple and fast synthesis steps, but also provides great stereoselectivity and productivity, thereby being capable of lowering the technical threshold and cost of synthesis, and meeting the green chemical concept advocated currently.

BRIEF DESCRIPTION OF THE DRAWINGS

None.

DETAILED DESCRIPTION OF THE PREFERRED EMBODIMENTS

The detailed description and technical content of the present invention are illustrated hereafter in connection with experiments:

The present invention provides a method for synthesizing tetrahydroisoquinoline thiazolidine, in which a compound 1a and a compound 1b are reacted at a temperature between 20° C. and 100° C. in a solvent, wherein the compound 1a comprises a structure of Formula (I), and the compound 1b comprises a structure of Formula (II).

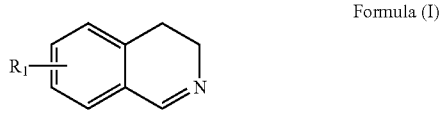

Formula (I)

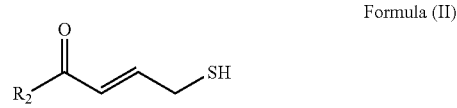

Formula (II)

In the present invention, $R_1$ is selected from the group consisting of hydrogen, halogen, an alkyl group, and an alkoxy group; and $R_2$ is selected from the group consisting of an alkoxy group, an aryloxy group, and N(OMe)Me, wherein Me is a methyl group. For example, the halogen may be fluorine, chlorine, bromine, iodine and the like; the alkyl group may be an alkyl group comprising 1 to 2 carbon atoms, such as methyl, ethyl and the like; and the alkoxy group may be an alkoxy group comprising 1 to 2 carbon atoms, such as a methoxy group (—OCH3), an ethoxy group (—OCH2CH3) and the like.

In the present invention, the solvent is selected from the group consisting of tetrahydrofuran (THF), ethyl acetate (EtOAc), acetone, ethanol, dichloromethane (DCM), acetone, and acetonitrile.

In an embodiment of the present invention, the compound 1a and the compound 1b are reacted to form a compound 1c of Formula (III) and a compound 1d of Formula (IV), wherein the compound 1c and the compound 1d are diastereomers.

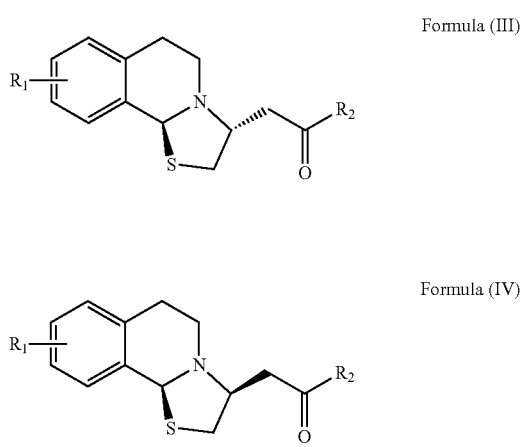

Formula (III)

Formula (IV)

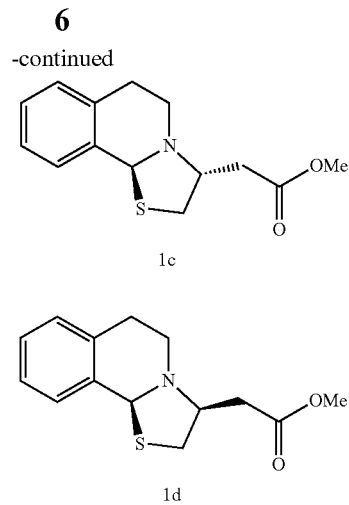

1c

1d

In an embodiment of the present invention, the ratio of the compound 1c of Formula (III) to the compound 1d of Formula (IV) is approximately between 2:1 and 4:1. For example, in an embodiment the ratio of the compound 1c of Formula (III) to the compound 1d of Formula (IV) is about 3:1.

In an embodiment of the present invention, the compound 1a and the compound 1b are reacted with an equivalent ratio of 1:1.

During the synthesis process of the present invention, an acidic additive is further added to shorten the reaction time and increase the productivity. A specific example of the acidic additive is acetic acid (AcOH).

In an embodiment of the present invention, the reaction can be carried out under reflux to maintain a certain reaction temperature. However, the present invention is not limited to this, as long as the reaction is carried out at a temperature between 20° C. and 100° C. In other embodiments, the reaction can also be carried out at room temperature while a good productivity can still be obtained.

In an embodiment of the present invention, the time required for completing the synthesis may be between 30 minutes and 3 hours, between 1 hour and 2 hours, or even about 1 hour to complete the synthesis of tetrahydroisoquinoline thiazolidine.

The synthesis steps of the present invention will be illustrated in details in connection with examples hereafter.

Experiment Example 1

Firstly, a compound 1a (which is an isoquinoline) and a compound 1b (which is a α,β-unsaturated ester compound) were used as starting materials, and tetrahydrofuran (THF) was used as a solvent, to conduct a reaction at room temperature (rt).

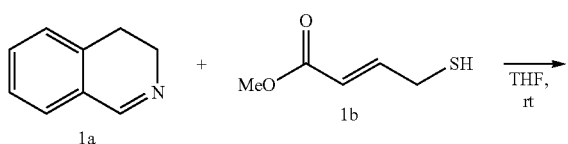

During the reaction process, by monitoring the reaction extent via paper chromatography and thin layer chromatography (TLC), it was found that it was required to take about 48 hours for the compound 1b to complete the reaction, with a yield of 52%.

In order to shorten the reaction time and improve the productivity, different kinds of additives were added during the reaction process, and the reaction time, the productivity and the product ratio of the compound 1c to the compound 1d were observed as shown in Table 1.

TABLE 1

| Group | Additive (equivalent) | Reaction Time (hour) | Productivity (%) | Compound 1c: Compound 1d |
| --- | --- | --- | --- | --- |
| 1 | NA | 48 | 52 | 3:1 |
| 2 | $K_2CO_3$ (1.0) | 48 | 50 | 3:1 |
| 3 | DMAP (1.0) | 48 | 53 | 3:1 |
| 4 | TEA (1.0) | 1 | 50 | 3:1 |
| 5 | AcOH (1.0) | 1 | 50 | 3:1 |
| 6 | AcOH (2.0) | 1 | 57 | 3:1 |
| 7 | AcOH (3.0) | 1 | 69 | 3:1 |
| 8 | HCOOH (3.0) | 1 | 60 | 3:1 |

As can be seen from Table 1, the addition of acidic additives such as formic acid (HCOOH) and acetic acid (AcOH) can shorten the reaction time to 1 hour, and especially after the addition of acetic acid (AcOH), not only the reaction time was shortened, but also the productivity was increased to 69%. However, the ratio of compound 1c to compound 1d was maintained at a ratio of about 3:1, without being affected by the types of additives used in Table 1.

Experiment Example 2

In this experiment example, a synthesis reaction was conducted by using the compound 1a and the compound 1b as starting materials in different solvents as shown in Table 2 below, and 3 equivalents of acetic acid (AcOH) was added as an additive. The aforementioned reaction was carried out in the same manner as in the Experimental Example 1 and at room temperature (rt), wherein the phrase "room temperature (rt)" is defined as a temperature between 25° C. and 28° C.

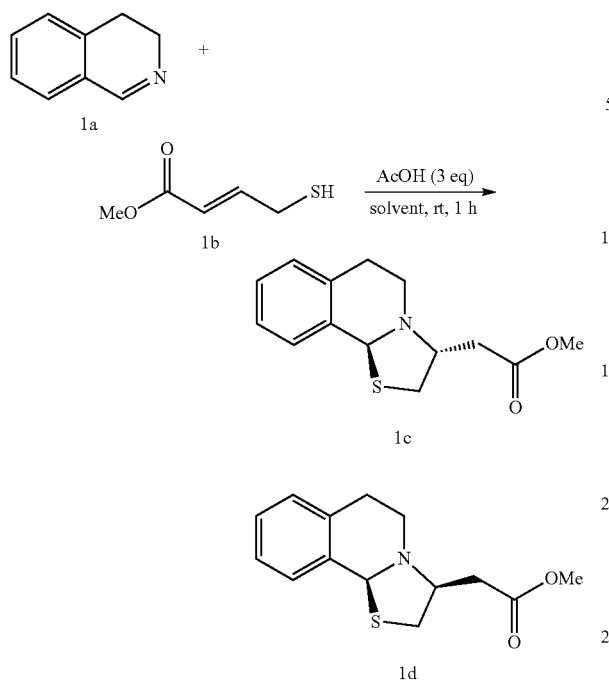

1a

1b

1c

1d

In this experimental example, the productivity and the ratio of the compound 1c to the compound 1d after addition of different types of solvents were observed, and the results were shown in Table 2 below.

TABLE 2

| Group | Solvent | Productivity (%) | Compound 1c: Compound 1d |
|---|---|---|---|
| 1 | tetrahydrofuran | 69 | 3:1 |
| 2 | ethyl acetate | 70 | 3:1 |
| 3 | ethanol | 62 | 3:1 |
| 4 | dichloromethane | 67 | 3:1 |
| 5 | acetone | 55 | 3:1 |
| 6 | acetonitrile | 50 | 3:1 |

The productivity was 63% to 70% when the solvent was ethyl acetate (EtOAc), ethanol (EtOH), or dichloromethane (DCM). When the reaction was carried out in acetonitrile, the productivity was slightly reduced to 50%, which is lower than those using tetrahydrofuran (THF) as the solvent.

In the Experimental Example 2, it was also observed that the ratio of compound 1c to compound 1d was maintained at about 3:1, without being influenced by the types of the solvents used in Table 2.

Experiment Example 3

In this experimental example, the compound 1a and the compound 1b were used as starting materials, ethyl acetate (EtOAc) was used as a solvent, and 3 equivalents of acetic acid (AcOH) was added as an additive. The reaction was carried out at different temperatures.

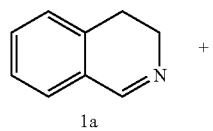

1a

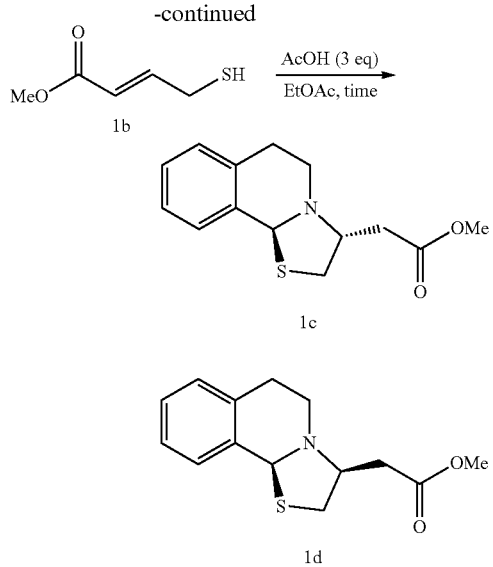

1b

1c

1d

After the aforementioned reaction, the productivity and the ratio of compound 1c to compound 1d were shown in Table 3 below.

TABLE 3

| Group | Temperature (° C.) | Time (hour) | Productivity (%) | Compound 1c: Compound 1d |
|---|---|---|---|---|
| 1 | rt | 1 | 70 | 3:1 |
| 2 | reflux | 1 | 85 | 3:1 |
| 3 | reflux | 2 | 86 | 3:1 |

As can be seen from Table 3 that, a good productivity (70%) had been achieved after a 1-hour reaction at room temperature (rt); and when reflux was used, the productivity was increased to 85% after the 1-hour reaction, and when the reaction time was increased to 2 hours under the same conditions, the productivity was 86%. However, in the Experiment Example 3, the ratio of compound 1c to compound 1d was also maintained at a ratio of about 3:1, without being affected by the temperature. The phrase "room temperature" is defined herein as a temperature between 25° C. and 28° C.; and the phrase "reflux" is defined as a temperature between 70° C. and 90° C.

Experiment Example 4

The reaction conditions in Experimental Example 4 were approximately the same as those in Experimental Example 3. However, in Experimental Example 4, the ratio of the two starting materials was changed and it was observed whether or not the productivity could thus be improved as shown in Table 4.

TABLE 4

| Group | Compound 1a (equivalent) | Compound 1b (equivalent) | Productivity (%) | Compound 1c: Compound 1d |
|---|---|---|---|---|
| 1 | 1.0 | 1.0 | 85 | 3:1 |
| 2 | 1.0 | 1.5 | 82 | 3:1 |
| 3 | 1.0 | 2 | 80 | 3:1 |
| 4 | 1.0 | 4 | 60 | 3:1 |

When the equivalent of the compound 1b was slightly increased to 1.5 equivalents, the compound 1a was still remained and the productivity was not increased. The same result was obtained when the equivalent of the compound 1b was increased to 2 or 4 equivalents: the compound 1a still could not react completely and the productivity could not be improved.

In view of the above, in this experiment example, a better productivity (85%) was obtained when the compound 1a and the compound 1b were reacted with 1:1 equivalent as starting materials.

Experiment Example 5

The reaction conditions in the Experimental Example 5 were approximately the same as those in the Experimental Example 4, wherein 1 equivalent of the compound 1a and 1 equivalent of the compound 1b were used as starting materials, the solvent was ethyl acetate (EtOAc), 3 equivalents of acetic acid (AcOH) was added as an additive, and the reaction was heated under reflux for one hour. The difference from the Experimental Example 4 was that the Experimental Example 5 was conducted by reacting the compound 1a comprising a different substituent group $R_1$ and the compound 1b having a different substituent group $R_2$.

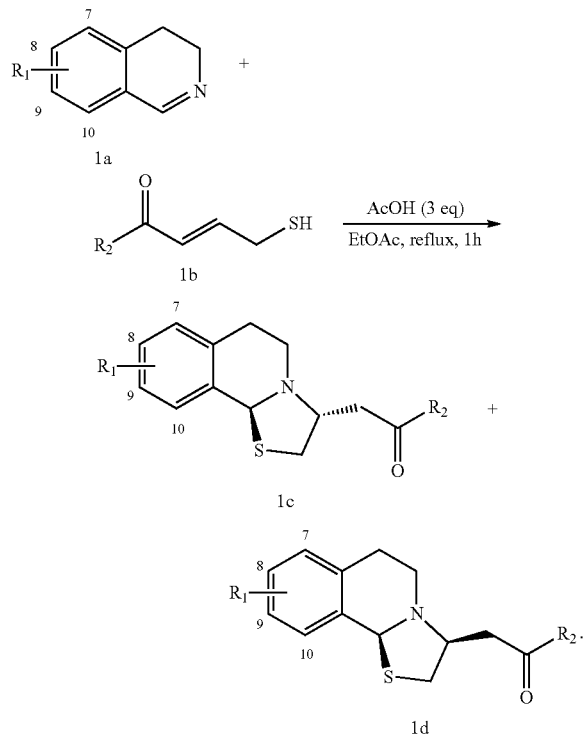

With respect to the substituent groups $R_1$ and $R_2$, the productivity, and the ratio of the compound 1c to the compound 1d, the results were as shown in Table 5 below.

TABLE 5

| Group | $R_1$ | $R_2$ | 1c | Productivity (%) | Compound 1c: Compound 1d |
|---|---|---|---|---|---|
| 1 | H | OMe | 212a | 85 | 3.6:1 |
| 2 | 9-Cl | OMe | 212b | 79 | 2.5:1 |

TABLE 5-continued

| Group | $R_1$ | $R_2$ | 1c | Productivity (%) | Compound 1c: Compound 1d |
|---|---|---|---|---|---|
| 3 | 8-Br | OMe | 212c | 83 | 2.5:1 |
| 4 | 8-OMe | OMe | 212d | 63 | 2.5:1 |
| 5 | 8,9-OMe | OMe | 212e | 87 | 3.5:1 |
| 6 | H | OEt | 212f | 83 | 3:1 |
| 7 | 9-OMe | OEt | 212g | 67 | 3:1 |
| 8 | —Br | OEt | 212h | 87 | 2.5:1 |
| 9 | 9-F | OEt | 212i | 81 | 3.5:1 |
| 10 | 9-Me | OEt | 212j | 84 | 3:1 |
| 11 | H | OBn | 212k | 81 | 4:1 |
| 12 | 7-Cl | OBn | 212l | 80 | 3.7:1 |
| 13 | 9-Cl | OBn | 212m | 79 | 4:1 |
| 14 | 8-OMe | OBn | 212n | 70 | 4:1 |
| 15 | H | N(OMe)Me | 212o | 70 | 3.4:1 |
| 16 | 7-F | N(OMe)Me | 212p | 61 | 3:1 |
| 17 | 9-Cl | N(OMe)Me | 212q | 60 | 3:1 |

The reaction tests were carried out respectively by using the eighth and the ninth carbon atoms on the structure of the compound 1a as electron-withdrawing substituent groups, and the generated corresponding compounds 1c were respectively named as 212b and 212c, with productivities of respectively 79% (group 2) and 83% (group 3). However, when the eighth carbon atom on the structure of the compound 1a was a methoxyl group (OMe), the reactivity was slightly poor when the compound 1c (named as 212d) was generated, and the productivity was decreased to 63% (group 4). Additionally, the compound 1c named as 212e was also successfully obtained with a productivity of 87% when the compound 1a bis-substituted at the eighth and the ninth carbon atoms with methoxy groups was used for reaction (group 5).

When the compound 1b comprising a substituent group $R_2$ of —OEt (ethoxyl group) was reacted with the compound 1a comprising different substituent groups, it was found that when the substituent group $R_1$ of the compound 1a was halogen, the compound 1c in expectation (named as 212h and 212i) were generated with productivities of 87% (group 8) and 81% (group 9), respectively; when the $R_1$ was changed from a halogen substituent group to a methoxyl group, the productivity was decreased to 67%, and thus when a methyl group being also an electron-donating group was used, the compound 1c named as 212j with a productivity of 84% (group 10) was obtained.

Substantially, the compound 1b comprising the substituent group $R_2$ of —OBn (aryloxy group) was reacted with the compound 1a comprising different types of substituent groups. When the reaction was carried out by using the compound 1a substituted with halogen at the eight and the ninth carbon, the compounds 1c respectively named as 212l and 212m were obtained with the productivity performance of about 80% (group 12 and group 13), and when the substituent group of the compound 1a was the methoxy group, the productivity was slightly lower as compared with the aforementioned other substituent groups.

Finally, the compound 1b comprising the substituent group $R_2$ of —N(OMe)Me was reacted with the compound 1a comprising different substituent groups, such that the generated corresponding thiazolidine compounds of compound 1c had a slightly lower productivity of 70-60% (named as 212o -212q, for groups 15 to 17).

With respect to each of the different thiazolidine compounds synthesized in this experimental example, the diastereoselectivity ratio of the compound 1c in expectation to the compound 1d was 3:1, and the ratio was not changed due to changing of substituent groups of the compounds 1a and 1b. However, a good productivity was obtained regardless of whether there was an electron withdrawing group or an electron donating group on the molecular structure of the compound 1a, except when the substituent group was the methoxy group.

In view of the above, as compared with the prior art which obtained thiazolidine compounds with a satisfactory yield only in a strict environment or after a long time is spent, the method provided by the present invention not only has milder synthesis conditions, simple and fast synthesis steps, but also has great stereoselectivity and productivity, thereby being capable of lowering the technical threshold and cost of synthesis, and meeting the green chemical concept advocated currently.

What is claimed is:

1. A method for synthesizing tetrahydroisoquinoline thiazolidine of formula (III) and formula (IV):

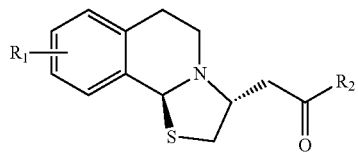

Formula (III)

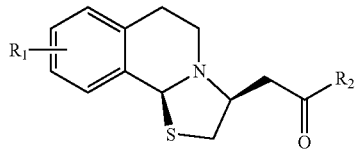

Formula (IV)

comprising reacting, at a temperature between 20° C. and 100° C. in a solvent, a compound of Formula (II) and a compound of Formula (I):

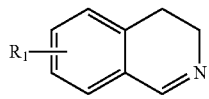

Formula (I)

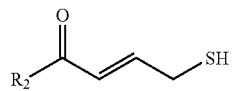

Formula (II)

wherein, $R_1$ is selected from the group consisting of hydrogen, halogen, an alkyl group, and an alkoxy group;

$R_2$ is selected from the group consisting of an alkoxy group, an aryloxy group, and N(OMe)Me, wherein Me is a methyl group; and the solvent is selected from the group consisting of tetrahydrofuran (THF), ethyl acetate (EtOAc), ethanol, dichloromethane (DCM), acetone, and acetonitrile.

2. The method for synthesizing tetrahydroisoquinoline thiazolidine of claim 1, wherein a ratio of the compound of Formula (III) to the compound of Formula (IV) is between 2:1 and 4:1.

3. The method for synthesizing tetrahydroisoquinoline thiazolidine of claim 1, wherein the compound of Formula (I) and the compound of Formula (II) are reacted in a ratio of 1:1.

4. The method for synthesizing tetrahydroisoquinoline thiazolidine of claim 1, further comprising an acidic additive.

5. The method for synthesizing tetrahydroisoquinoline thiazolidine of claim 4, wherein the acidic additive is acetic acid (AcOH).

6. The method for synthesizing tetrahydroisoquinoline thiazolidine of claim 1, wherein the method is carried out under reflux.

7. The method for synthesizing tetrahydroisoquinoline thiazolidine of claim 1, wherein the method has a reaction time between 30 minutes and 3 hours.

* * * * *